United States Patent [19]

Bryant et al.

[11] Patent Number: 5,760,030
[45] Date of Patent: Jun. 2, 1998

US005760030A

[54] BENZOTHIOPHENE COMPOUNDS AND METHODS OF USE

[75] Inventors: Henry Uhlman Bryant, Indianapolis; George Joseph Cullinan, Trafalgar; Kennan Joseph Fahey, Indianapolis, all of Ind.

[73] Assignee: Eli Lilly and Company, Indianapolis, Ind.

[21] Appl. No.: 886,575

[22] Filed: Jun. 30, 1997

[51] Int. Cl.$^6$ .................... A61K 31/38; A61K 31/44; C07D 409/00; C07D 411/00

[52] U.S. Cl. .................... 514/213; 514/324; 514/422; 514/444; 540/596; 546/202; 548/527; 549/51; 549/57

[58] Field of Search .................... 546/202; 514/324, 514/422, 213, 444; 548/527; 540/596; 549/51, 57

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones | 424/267 |
| 4,656,187 | 4/1987 | Black et al. | 514/422 |
| 5,395,842 | 3/1995 | Labrie | 514/320 |
| 5,470,854 | 11/1995 | Angerer et al. | 514/233 |
| 5,472,962 | 12/1995 | Koizumi et al. | |
| 5,484,798 | 1/1996 | Bryant et al. | 514/324 |
| 5,514,703 | 5/1996 | Carlson et al. | 514/443 |
| 5,514,704 | 5/1996 | Carlson et al. | 514/443 |
| 5,521,214 | 5/1996 | Bryant et al. | 514/443 |
| 5,532,254 | 7/1996 | Bowling | 514/320 |
| 5,532,382 | 7/1996 | Carlson et al. | 549/57 |
| 5,567,828 | 10/1996 | Dodge | 549/51 |

FOREIGN PATENT DOCUMENTS

| | | |
|---|---|---|
| 062 503 | 10/1982 | European Pat. Off. . |
| WO 89/02893 | 4/1989 | WIPO . |
| WO 95/10513 | 4/1995 | WIPO . |

OTHER PUBLICATIONS

Crenshaw, R.R., et al, *J. Med. Chem.* 14(12):1185–1190 (1971).
Jones, C.D., et al, *J. Med. Chem.* 27: 1057–1066, 1984.
Jones, C.D., et al, *J. Med. Chem.* 35: 931–938 1992.

*Primary Examiner*—Mukund J. Shah
*Assistant Examiner*—Bruck Kifle
*Attorney, Agent, or Firm*—Janelle D. Strode; David E. Boone

[57] ABSTRACT

The instant invention provides novel benzothiophene compounds, pharmaceutical formulations, and methods of use.

19 Claims, No Drawings

BENZOTHIOPHENE COMPOUNDS AND METHODS OF USE

FIELD OF THE INVENTION

This invention relates to the fields of pharmaceutical and organic chemistry and provides novel benzo[b]thiophene compounds which are useful for the treatment and prevention of various medical indications associated with estrogen deprivation, postmenopausal syndrome, estrogen-dependent cancer, uterine fibroid disease, endometriosis, and arterial smooth muscle cell proliferation, also known as restenosis.

BACKGROUND OF THE INVENTION

Estrogen deprivation in a subject may occur through a variety of means, including but not limited to ovariectomy and menopause, and typically results in a number of related health concerns. "Postmenopausal syndrome" is a term used to describe various pathological conditions which frequently affect women who have entered into or completed the physiological metamorphosis known as menopause. Numerous pathologies are contemplated by the use of this term, with major effects of postmenopausal syndrome including but not limited to osteoporosis, cardiovascular effects such as hyperlipidemia, and estrogen-dependent cancer, particularly breast and uterine cancer.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

In response to the clear need for new pharmaceutical agents which are capable of alleviating the symptoms of, inter alia, postmenopausal syndrome, the present invention provides benzo[b]thiophene compounds, pharmaceutical formulations thereof, and methods of using such compounds for the treatment of postmenopausal syndrome and other estrogen-related pathological conditions such as those mentioned below.

Another major estrogen associated pathology is estrogen-dependent breast cancer and, to a lesser extent, estrogen-dependent cancers of other organs, particularly the uterus. Although such neoplasms are not solely limited to a post-menopausal woman, they are more prevalent in the older, postmenopausal population. Current chemotherapy of these cancers have relied heavily on the use of anti-estrogen compounds, such as tamoxifene. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be counterproductive in some cases. A better therapy for the treatment of these cancers would be an agent which is an antiestrogenic compound having fewer or no estrogen agonist properties on reproductive tissues.

Uterine fibrosis (uterine fibroid disease) is a clinical problem which goes under a variety of names, including uterine hypertrophy, fibrosis uteri, and uterine lieomyomata, myometrial hypertrophy, and uterine metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood, but evidence suggests that it is an inappropriate response of fibroid tissue to estrogen. Such a condition has been produced in rabbits by daily administrations of estrogen for three months. In guinea pigs, the condition has been produced by daily administration of estrogen for four months. In rats, estrogen causes similar hypertrophy.

The most common treatment of uterine fibrosis involves surgical procedures both costly and sometimes a source of complications due to the formation of abdominal adhesions and infection. In some patients, initial surgery is only a temporary treatment and the fibroids regrow. In those cases a hysterectomy is performed which effectively ends the fibroids but also the reproductive life of the patient. Also, gonadotropin-releasing hormone antagonists may be administered, yet their use is tempered by the fact that they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity, and often leads to infertility. The cause of the symptoms of this condition appear to be ectopic endometrial growths which respond to normal hormonal control (cycling), but are located in inappropriate tissues. Because of the inappropriate locations for endometrial growth, the tissues seem to initiate local inflammatory responses causing macrophage infiltration and a cascade of events leading to a painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen. However, it is sometimes necessary to use estrogen continuously to control the symptoms. This use of estrogen can often lead to undesirable side effects and even to the risk of endometrial cancer.

Another treatment consists of continuous administration of progestins which induces amenorrhea by suppressing ovarian estrogen production, but can cause regressions of the endometrial growths. The use of chronic progestin therapy is often accompanied by the unpleasant CNS side effects of progestins, and often leads to infertility due to suppression of ovarian function.

A third treatment consists of the administration of weak androgens, which are effective in controlling the endometriosis. However, they also induce severe masculinization. Continued use of several of these treatments for endometriosis have also been implicated in mild bone loss. Therefore, new methods of treating endometriosis are desirable.

Smooth muscle cell proliferation plays an important role in diseases such as atherosclerosis and restenosis. Vascular restenosis after percutaneous transluminal coronary angioplasty (PTCA) has been shown to be a tissue response characterized by an early and a late phase. The early phase occurring hours to days after PTCA is due to thrombosis with some vasospasms, while the late phase appears to be dominated by excessive proliferation and migration of vascular aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism of the reocclusion of coronary arteries following PTCA, laser angioplasty, and arterial bypass graft surgery. (See: "Intimal Proliferation of Smooth Muscle Cells as an Explanation for Recurrent Coronary Artery Stenosis after Percutaneous Transluminal Coronary Angioplasty", Austin et al., *Journal of the American College of Cardiology,* 8:369–375 (August 1985)).

Vascular restenosis remains a major long term complication following surgical intervention of blocked arteries by PTCA, atherectomy, laser angioplasty, and arterial bypass graft surgery. In about 35% of the patients who undergo PTCA, reocclusion occurs within three to six months after the procedure. The current strategies for treating vascular restenosis include mechanical intervention by devices such as agents or pharmacologic therapies including heparin, low molecular weight heparin, coumarin, aspirin, fish oil, calcium antagonists, steroids, and prostacyclin. These strategies have failed to curb the reocclusion rate and have been ineffective for the treatment and prevention of vascular restenosis. (See: "Prevention of Restenosis after Percutaneous Transluminal Coronary Angioplasty: The Search for a 'Magic Bullet'", Hermans et al., *American Heart Journal,* 122:171–187 (July 1991)).

In the pathogenesis of restenosis, excessive cell proliferation and migration occurs as a result of growth factors produced by cellular constituents in the blood and in the damaged arterial vessel wall which mediate the proliferation of smooth muscle cells in vascular restenosis. Agents that inhibit the proliferation and/or migration of smooth aortal muscle cells are useful in the treatment and prevention of restenosis. The present invention provides for the use of these compounds as smooth aortal muscle cell proliferation inhibitors and thus, as inhibitors of restenosis.

Thus, it would be a significant contribution to the art to provide novel benzothiophene compounds useful, for example, in the treatment or prevention of the disease states as indicated herein.

SUMMARY OF THE INVENTION

The present invention provides compounds of formula I:

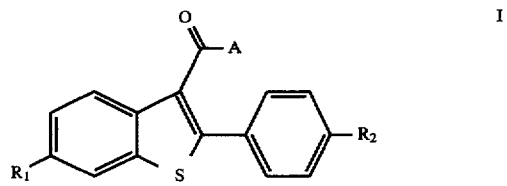

wherein:

$R_1$ is —H, —OH, —O($C_1$–$C_4$ alkyl), —O—CO—($C_1$–$C_6$ alkyl), —O—CO—O($C_1$–$C_6$ alkyl), —O—CO—Ar where Ar is phenyl or optionally substituted phenyl, —O—CO—O—Ar where Ar is phenyl or optionally substituted phenyl, or —OSO$_2$—($C_4$–$C_6$ alkyl);

$R_2$ is —H, —OH, —O($C_1$–$C_4$ alkyl), —O—CO—($C_1$–$C_6$ alkyl), —O—CO—O($C_1$–$C_6$ alkyl), —O—CO—Ar where Ar is phenyl or optionally substituted phenyl, —O—CO—O—Ar where Ar is phenyl or optionally substituted phenyl, —OSO$_2$—($C_4$–$C_6$ alkyl), —F, —Cl, or Br;

A is

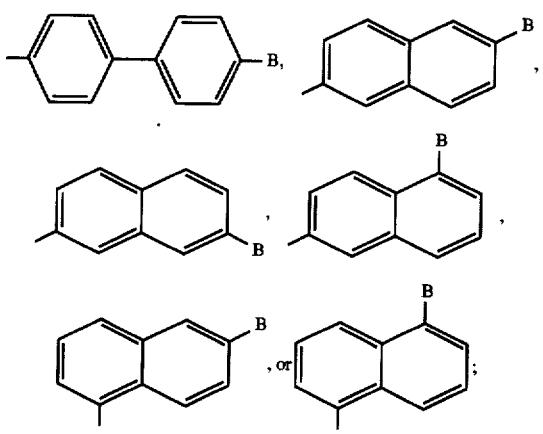

B is —OCH$_2$CH$_2$NR$_3$R$_4$;

R$_3$ and R$_4$ each are independently C$_1$–C$_4$ alkyl, or combine to form, with the nitrogen to which they are attached, piperidinyl, pyrrolidinyl, methylpyrrolidinyl, dimethylpyrrolidinyl, or hexamethyleneimino;

or a pharmaceutically acceptable salt or solvate thereof.

The present invention further provides pharmaceutical formulations containing compounds of formula I, optionally containing an effective amount of an additional therapeutic agent selected from the group consisting of estrogen, progestin, bisphosphonate, PTH, and subcombinations thereof, and the use of said compounds and/or subcombinations at least for the inhibition of estrogen deprivation, postmenopausal symptoms, particularly osteoporosis, cardiovascular-related pathological conditions including hyperlipidemia and related cardiovascular pathologies, and estrogen-dependent cancer.

The present invention still further provides pharmaceutically acceptable compositions comprising a compound of formula I and optionally additional therapeutic agents, along with pharmaceutically acceptable diluents or carriers.

The present invention also provides methods of use of the compounds of formula I for the inhibition of uterine fibrosis and endometriosis in women, and for the inhibition of aortal smooth muscle cell proliferation and restenosis in humans.

DETAILED DESCRIPTION OF THE INVENTION

General terms used in the description of compounds herein described bear their usual meanings. For example, "C$_1$–C$_4$ alkyl" refers to straight or branched aliphatic chains of 1 to 4 carbon atoms including methyl, ethyl, propyl, iso-propyl, n-butyl, and the like; and "C$_1$–C$_6$ alkyl" encompasses the groups included in the definition of "C$_1$–C$_4$ alkyl" in addition to groups such as pentyl, iso-pentyl, hexyl, and the like.

The term "substituted phenyl" refers to a phenyl group having one or more substituents selected from the group consisting of C$_1$–C$_4$ alkyl, C$_1$–C$_3$ alkoxy, hydroxy, nitro, chloro, fluoro, tri(chloro or fluoro)methyl, and the like. "C$_1$–C$_4$ alkoxy" refers to a C$_1$–C$_4$ alkyl group attached through an oxygen bridge, such as methoxy, ethoxy, n-propoxy, and isopropoxy, butoxy, and the like. Of these C$_1$–C$_4$ alkoxy groups, methoxy is highly preferred.

The term "inhibit" includes its generally accepted meaning which includes prohibiting, preventing, restraining, and slowing, stopping, or reversing progression, severity, or ameliorating a resultant symptom or effect.

A preferred embodiment of the current invention is [2-(4-hydroxyphenyl)-6-hydroxybenzo[b]thien-3-yl][4'-[2-(1-piperidinyl)ethoxy]biphenyl-4-yl]methanone hydrochloride, for example, where R$_1$ and R$_2$ are hydroxy, R$_3$ and R$_4$ combine to form, with the nitrogen to which they are attached, a piperidinyl ring, A is biphenyl, and the hydrochloride salt thereof.

Another preferred embodiment of the current invention is [2-(4-hydroxyphenyl)-6-hydroxybenzo[b]thien-3-yl][6-[2-(1-piperidinyl)ethoxy]naphth-2-yl]methanone, for example, where R$_1$ and R$_2$ are hydroxyl, R$_3$ and R$_4$ combine to form, with the nitrogen to which they are attached, a piperidinyl ring, A is a 2,6-disubstituted naphthyl, and the hydrochloride salt thereof.

Illustrative compounds of the invention are

[2-(4-Methoxyphenyl)-6-methoxybenzo[b]thien-3-yl][4'-[2-(1-piperidinyl)ethoxy]biphenyl-4-yl]methanone.
[2-(4-Hydroxyphenyl)-6-hydroxybenzo[b]thien-3-yl][4'-[2-(1-piperidinyl)ethoxy]biphenyl-4-yl]methanone.
[2-(4-Methoxyphenyl)-6-methoxybenzo[b]thien-3-yl][6-[2-(1-piperidinyl)ethoxy]naphth-2-yl]methanone, and
[2-(4-Hydroxyphenyl)-6-hydroxybenzo[b]thien-3-yl][6-[2-(1-piperidinyl)ethoxy]naphth-2-yl]methanone.

The compounds of this invention are derivatives of benzo[b]thiophene, which are named and numbered according to the Ring Index, The American Chemical Society, as follows:

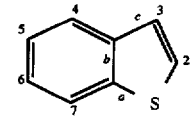

The compounds of the present invention, for example, compounds of formula I, may be synthesized essentially as described in U.S. Pat. Nos. 4,133,814, 4,358,593, 4,418,068, 5,393,763, and 5,482,949, all of which are herein incorporated by reference.

Generally, a benzothiophene precursor of formula II may be prepared by procedures known in the art.

II

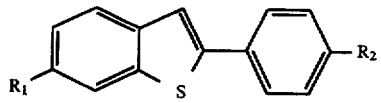

(wherein R$_1$ and R$_2$ are as previously defined.)

Following preparation of the desired presursor, compounds of formula II may be acylated at the 3-position of the benzothiophene nucleus with activated carboxyl moieties of the compounds of formula IIIa and IIIb under standard Friedel-Crafts conditions.

IIIa

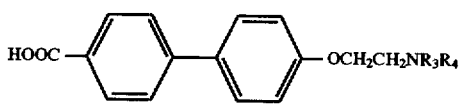

IIIb

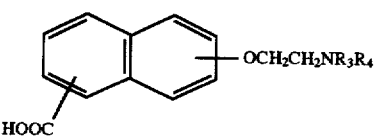

wherein: R$_3$ and R$_4$ have their previous meanings.

In general, the acylating conditions would be the use of a Lewis acid such as, AlCl$_3$, BF$_3$, and the like, in an appropriate solvent such as a halogenated hydrocarbon, such as for example methylene chloride, dichloroethane, and the like, at temperatures from 0°–100° C. The activated carboxyl moieties of the compounds of formulas IIIa and IIIb are acyl halides, mixed anhydrides, and the like, with the preferred being the acid chloride. The compounds of formula II may be prepared in accordance with the methods described in U.S. Pat. No. 4,133,814. It would be understood to those skilled in the art of organic chemistry that the ligands $R_1$ and $R_2$ must be compatible with the acylating conditions to form the compounds of formula I, thus a preferred intermediate would be where $R_1$ and $R_2$ are —OMe.

The compounds of formula IIIa and IIIb may be prepared by O-alkylation of their corresponding phenolic esters (formula IVa and IVb), for example, methyl or ethyl esters, with an appropriate halo-alkyl-amino side chain as provided in formula V.

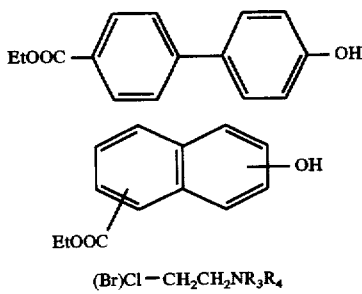

(Br)Cl—CH$_2$CH$_2$NR$_3$R$_4$      V wherein: $R_3$ and $R_4$ have their previous meanings.

The halogen of the compounds of formula V may be either —Cl or —Br, with —Cl being preferred. This alkylation is performed in the presence of a strong inorganic base, such as $K_2CO_3$, NaH, or the like, in an appropriate solvent, such as for example DMF, at an elevated temperature. The ethyl ester protecting group may be removed by hydrolysis in base to yield the compounds of formula IIIa or IIIb.

The compounds of formula IVa and IVb may be prepared by esterification of their corresponding acids with the appropriate alcohol by methods known in the art. The phenolic acids of formula IVa and IVb are either commercially available or can be derived by methods known in the art, for example, various hydroxy naphthoic acids are provided in Dewar, J. S. and Grisdale, P. J., *J. Am. Chem. Soc.*, 84, p. 3541-6 (1962), the disclosure of which is herein incorporated by reference.

Other compounds of formula I where $R_1$ and $R_2$ are esters or sulfonates may be derived from demethylation of the dimethoxy compound with AlCl$_3$/EtSH, BCl$_3$, and the like, followed by acylation with the appropriate acyl or sulfonyl moiety. Although the free-base form of formula I compounds can be used in the methods of the present invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means.

Further, the present invention provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the present invention which is capable of inhibiting, alleviating, ameliorating, treating, or preventing further symptoms in mammals, including humans, suffering from estrogen deprivation, for example, menopause or ovariectomy, or inappropriate estrogen stimulation such as uterine fibrosis or endometriosis, or suffering from aortal smooth muscle cell proliferation or restenosis. In the case of estrogen-dependent cancers, the term "effective amount" means the amount of compound of the present invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 20 mg to 1000 mg, and more typically from 20 mg and 100 mg. Such dosages will be administered to a patient in need of treatment from one to three times each day or as often as needed for efficacy.

The present invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed infra. The present invention contemplates and encompasses such maladies although not specified by name.

As a further embodiment of the invention, the compounds of formula I may be administered along with an effective amount of an additional therapeutic agent, including but not limited to estrogen, progestin, other benzothiophene compounds including raloxifene, bisphosphonate compounds such as alendronate and tiludronate, parathyroid hormone (PTH), including truncated and/or recombinant forms of PTH such as, for example, PTH (1-34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-α-ethynyl estradiol (0.01–0.03 mg/day), mestranol (0.05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are preferred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

| Formulation 1: Gelatin Capsules | |
| --- | --- |
| Ingredient | Quantity (mg/capsule) |
| Active Ingredient | 20–100 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

| Formulation 2: Tablets | |
| --- | --- |
| Ingredient | Quantity (mg/tablet) |
| Active Ingredient | 20–100 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

| Formulation 3: Aerosol | |
| --- | --- |
| Ingredient | Weight % |
| Active Ingredient | 0.50 |
| Ethanol | 29.50 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension
Suspensions each containing 100 mg of a compound of formula I per 5 mL dose.

| Ingredient | Weight |
| --- | --- |
| Active Ingredient | 50 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following examples and preparations are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

Preparation 1

4'-Hydroxy-biphenyl-4-methylcarboxylate 5 g (23.4 mmol) of 4'-hydroxy-biphenyl-4-carboxylic acid was dissolved in 150 mL of MeOH and 2 mL of conc. $H_2SO_4$. The reaction mixture was heated to reflux for twenty-four hours under a nitrogen atmosphere. Upon cooling, a precipitate formed which was removed by filtration. The precipitated was washed 150 mL of cold MeOH and dried in vacuo. This yielded 4.7 g of the title compound as a tan amorphous powder.
PMR: Consistent with the proposed structure.

Preparation 2

4'-[2-(1-Piperidinyl)ethoxy]biphenyl-4-methylcarboxylate hydrochloride 2 g (8.77 mmol) of 4'-hydroxy-biphenyl-4-methylcarboxylate was dissovled in 250 mL of methylethylketone and 1.84 g (10.8 mmol) of 2-(1-piperidinyl)chloroethane hydrochloride and 4.15 g (30.1 mmol) of $K_2CO_3$ were added. The reaction mixture was heated to reflux under a nitrogen atmosphere for forty-eight hours. The reaction was allowed to cool and filtered. The solution was evaporated and the product purified by chromatography on a silica gel column eluted with $CHCl_3$—MeOH (19:1) (v/v). The desired fraction were determined by tlc, combind, and evaporated to dryness. The solid was dissolved in 25 mL of MeOH and 5N HCl was added until a white precipitate stopped forming. The precipitate was filtered and crystallized from MeOH/ether. This yielded 2.8 g of the title compound as white powder.
PMR: Consistent with the proposed structure.
MS: m/e=339 (M–Cl) FD
EA: Calc: C, 67.10; H, 6.97; N, 3.73 Fd: C, 66.89; H, 6.70; N, 3.59 $C_{21}H_{25}NO_3$—HCl

Preparation 3

4'-[2-(1-Piperidinyl)ethoxy]biphenyl-4-carboxylic acid hydrochloride 2.8 g (7.48 mmol) of 4'-[2-(1-piperidinyl)ethoxy]biphenyl-4-methylcarboxylate hydrochloride was dissolved in 200 mL of MeOH and 75 mL of 1N NaOH was added. The reaction mixture was refluxed for two hours. The reaction was allowed to cool and the volume reduced by one-half by evaporation. The reaction mixture was cooled to 0° C. and 20 mL of 5N HCl was added. A white precipitate formed and was removed by filtration. The product was further purified by crystallization from hot MeOH. This yielded 1.8 g of the title compound as a white powder.
PMR: Consistent with the proposed structure.
MS: m/e=325 (M–Cl) FD
EA: Calc: C, 66.38; H, 6.69; N, 3.87 Fd: C, 66.44; H, 6.61; N, 3.89 $C_{20}H_{23}NO_3$—HCl

Example 1

[2-(4-Methoxyphenyl)-6-methoxybenzo[b]thien-3-yl][4'-[2-(1-piperidinyl)ethoxoy]biphenyl-4-yl] methanone 1.8 g (5 mmol) of 4'-[2-(1-Piperidinyl)ethoxy]biphenyl-4-carboxylic acid hydrochloride was dissolved in 50 mL of $CH_2Cl_2$ and 20 mL of thionyl chloride and one drop of DMF were added. The reaction mixture was refluxed for sixteen hours and evaporated to an oily solid. The oily solid was dissolved in 30 mL of $CH_2Cl_2$ and added to a stirring mixture of 550 mg (2.04 mmol) of 2-(4-methoxyphenyl)-6-methoxybenzo[b]thiophene in 75 mL of $CH_2Cl_2$ and the solution was cooled to 0° C. Over a period of twenty minutes, 1.01 g (7.6 mmol) of $AlCl_3$ was added. The reaction was allowed to continue for one hour under a nitrogen atmosphere at 0° C. The reaction was quenched by pouring into ice-water and organic phase was separated. The organic layer was washed with 150 mL of 1N NaOH, three times with 150 mL of brine, and finally twice with 150 mL of water. The solution was dried by filtration through anhydrous $Na_2SO_4$ and was chromatographed on a silica gel column eluted with a linear gradient beginning with $CHCl_3$ and ending with $CHCl_3$—MeOH (19:1) (v/v). The desired fractions were collected and evaporated to dryness. This yielded 1.05 g of the title compound as an amorphous solid.
PMR: Consistent with the proposed structure.

Example 2

[2-(4-Hydroxyphenyl)-6-hydroxybenzo[b]thien-3-yl][4'-[2-(1-piperidinyl)ethoxy]biphenyl-4-yl] methanone hydrochloride 1.05 g (1.7 mmol) of [2-(4-methoxyphenyl)-6-methoxybenzo[b]thien-3-yl][4'-[2-(1-piperidinyl)ethoxoy]

biphenyl-4-yl]methanone was dissolved in 50 mL of $CH_2Cl_2$ and cooled to 0° C. 1.21 g (9.1 mmol) of $AlCl_3$ was added and the reaction mixture was stirred for five minutes. 5 mL of EtSH was added and the reaction mixture was heated to reflux under a nitrogen atmosphere. After 2.5 hours, 25 mL of THF was slowly added and 30 mL of 20% aqueous HCl was slowly added keeping the temperature below 20° C. The reaction mixture was filtered and evaporated to a solid. The product was purified by chromatography on a silica gel column eluted with a gradient beginning with $CHCl_3$ and ending with $CHCl_3$—MeOH (23:2) (v/v). The desired fractions were evaporated to dryness and the product was crystallized from MeOH. This yielded 640 mg of the title compound as a light yellow powder.

PMR: Consistent with the proposed structure.
MS: m/e=550 (M—Cl) FD
EA: Calc: C, 69.67; H, 5.50; N, 2.39 Fd: C, 70.55; H, 5.57; N, 2.32 $C_{34}H_{33}NO_4$—HCl Preparation 4

6-Hydroxy-2-ethyl-naphthylate 10 g (53.2 mmol) of 6-hydroxy-2-naphthoic acid was dissolved in 600 mL of EtOH and 3 mL of conc. $H_2SO_4$ was added. The reaction mixture was refluxed for forty-eight hours, allowed to cool, and evaporated to dryness. The solid was dissolved in 300 mL of EtOAc. The EtOAc solution was washed four times with water, dried with $Na_2SO_4$ and evaporated to dryness. The product was crystallized from EtOAc-hexane. This yielded 8.7 g of the title compound as a yellow solid.

PMR: Consistent with the proposed structure.

Preparation 5

6-[2-(1-Piperidinyl)ethoxy]-2-ethyl-naphthylate 2.8 g (70 mmol) of NaH was suspended in 100 mL of DMF and cooled to 0° C. 12.8 g (69.4 mmol) of 2-(1-piperidinyl)chloroethane hydrochloride was added and stirred for twenty minutes. This solution was added to a solution of 5 g (23.1 mmol) of 6-hydroxy-2-ethyl-naphthylate in 75 mL of DMF at 0° C. An additional 1 g (41.6 mmol) of NaH was added and the reaction mixture was allowed to warm to ambient temperature. The reaction was allowed to proceed for sixteen hours. The reaction was quenched with MeOH and evaporated to an oil. The product was chromatographed on a silica gel column eluted with a linear gradient beginning with $CHCl_3$ and ending with $CHCl_3$—MeOH (9:1) (v/v). The desired fractions were obtained, combined, and evaporated to dryness. This yielded 5.63 g of the title compound as a solid.

PMR: Consistent with the proposed structure.

Preparation 6

6-[2-(1-Piperidinyl)ethoxy]naphthoic acid hydrochloride

In a manner similar to that used in Example 3, the title product was obtained in 59.7% yield as a tan powder.

PMR: Consistent with the proposed structure.
MS: m/e=300 (M—Cl) FD
EA: Calc: C, 64.38; H, 6.60; N, 4.17 Fd: C, 64.10; H, 6.65; N, 4.04. $C_{18}H_{21}NO_3$—HCl Example 3

[2-(4-Methoxyphenyl)-6-methoxybenzo[b]thien-3-yl][6-[2-(1-piperidinyl)ethoxy]naphth-2-yl]methanone In a manner similar to that used in Example 1, 2 g (6 mmol) of 6-[2-(1-piperidinyl)ethoxy]naphthoic acid hydrochloride and 1.1 g (4 mmol) of 2-(4-methoxyphenyl)-6-methoxybenzo[b]thiophene were converted to 1.4 g of the title compound as a tan amorphous solid.

PMR: Consistent with the proposed structure.

Example 4

[2-(4-Hydroxyphenyl)-6-hydroxybenzo[b]thien-3-yl][6-[2-(1-piperidinyl)ethoxy]naphth-2-yl]methanone In a manner similar to that used in Example 2, 1.4 g (2.54 mmol) of [2-(4-methoxyphenyl)-6-methoxybenzo[b]thien-3-yl][6-[2-(1-piperidinyl)ethoxy]naphth-2-yl]methanone, 1.4 g (10.2 mmol) of $AlCl_3$, and 2 mL (12.7 mmol) of EtSH was converted to 570 mg of the title compound as a yellow powder.

PMR: Consistent with the proposed structure.
MS: m/e=523 (M+) FD
EA: Calc: C, 73.40; H, 5.58; N, 2.67 Fd: C, 73.44; H, 5.77; N, 2.49. $C_{32}H_{29}NO_4S$.

The following discussions illustrate methods of use for the compounds of formula I in experimental models or in clinical studies. These examples are for the purposes of illustration and are not meant to be limiting in any way.

Postmenopausal Syndrome
(Representative pathologies associated with estrogen deprivation)

A. Osteoporosis:

Experimental models of postmenopausal osteoporosis are known in the art. Germane to this invention is the ovariectomized rat model which is provided in U.S. Pat. No. 5,393,763. The compounds of formula I would be active in this model and would demonstrate an effective treatment or prevention of bone loss due to the deprivation of estrogen.

An additional demonstration of the method of treating or preventing osteoporosis due to estrogen deprivation would be as follows: One hundred patients would be chosen, who are healthy postmenopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids six months prior to the study or who have ever taken bis-phosphonates.

Fifty women (test group) would receive 20–100 mg of a compound of formula I, for example, Formulation 1 (above), per day. The other fifty women (control group) would receive a matched placebo per day. Both groups would receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline crosslinks. Blood samples are measured for serum levels of osteocalcin and bone-specific alkaline phosphatase. Baseline measurements would also include a uterine examination and bone mineral density determination by photon absorptiometry.

The study would continue for six months, and each the patients would be examined for changes in the above parameters. During the course of treatment, the patients in the treatment group would show a decreased change in the biochemical markers of bone resorption as compared to the control group. Also, the treatment group would show little or no decrease in bone mineral density compared to the control group. Both groups would have similar uterine histology, indicating or compounds of formula I have little or no utrotrophic effects.

B. Hyperlipidemia:

Experimental models of postmenopausal hyperlipidemia are known in the art. Germane to this invention is the ovariectomized rat model which is detailed in U.S. Pat. No. 5,464,845.

Data presented in Table 1 show comparative results among ovariectomized rats, rats treated with 17-α-ethynyl estradiol ($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to estrogen is well recognized in the art.

Not only did the compounds of the present invention reduce serum cholesterol compared to the ovariectomized animals, but the uterine weight was increased to lesser extent than those given $EE_2$. Compared to estrogenic compounds known in the art, the benefit of serum cholesterol reduction while lessening the effect on uterine weight is unusual and desirable.

As expressed in the data below, estrogenicity also was assessed by evaluating the response of eosinophil infiltration into the uterus. The compounds of this invention did not cause as large an increase in the number of eosinophils observed in the stromal layer of the ovariectomized, rat uteri. $EE_2$ caused a substantial and expected increase in eosinophil infiltration.

The data presented in Table 1 reflect the response per treatment group.

TABLE 1

| Compound No. | Dose mg/kg[a] | Uterine Weight % Inc[b] | Uterine Eosinophil $(V_{max})$[c] | Serum Cholest. % Dec.[d] |
|---|---|---|---|---|
| $EE_2$ | 0.001 | 35.8* | 20* | −1.9 |
|  | 0.01 | 61.0* | 25.6* | 12 |
|  | 0.1 | 129.6* | 276.6* | 77.7* |
| 17-β-Estradiol | 0.001 | 74.1* | 13* | 67.6* |
|  | 0.01 | 48.5* | 9.8 | 57.5* |
|  | 0.1 | 83.8* | 29.8* | 58.7* |
| 5 | 0.01 | −16* | 3.7 | 15.9* |
|  | 0.1 | −10.6 | 2.9 | 66.7* |
|  | 1.0 | 108.7* | 292.9* | 87.3* |
| 10 | 0.1 | 1.4 | 7.1 | 39.4* |
|  | 1.0 | 10.7 | 6 | 59.3* |
|  | 10.0 | 57.6* | 47.0* | 69.1* |

[a]mg/kg PO
[b]Uterine Weight % increase versus the ovarierectomized controls
[c]Eoslnophil peroxidase, $V_{maximum}$
[d]Serum cholesterol decrease versus ovariectomized controls
*$p < .05$ An additional demonstration of the method of treating hyperlipidemia due to estrogen deprivation would be as follows: One hundred patients would be chosen, who are healthy postmenopausal women, aged 45–60, and who would normally be considered candidates for estrogen replacement therapy. This would include women with an intact uterus, who have not had a menstrual period for more than six months, but less than six years. Patients excluded for the study would be those who have taken estrogens, progestins, or corticosteroids.

Fifty women (test group) would receive 20–100 mg of a compound of formula I, for example, using Formulation 1, per day. The other fifty women (control group) would receive a matched placebo per day. The study would be a double-blind design. Neither the investigators nor the patients would know to which group each patient is assigned.

A baseline examination of each patient would include serum determination of cholesterol and triglyceride levels. At the end of the study period (six months), each patient would have their serum lipid profile taken. Analysis of the data would confirm a lowering of the serum lipids, for example, cholesterol and/or triglycerides, in the test group versus the control.

Provided below are further examples of estrogen-dependent pathologies demonstrating additional utilities of the instant compounds.

Estrogen-dependent Breast Cancer

A. MCF-7 Proliferation Assay Test Procedure

MCF-7 breast adenocarcinoma cells (ATCC HTB 22) are maintained in MEM (minimal essential medium, phenol-red free, Sigma St. Louis Mo.) supplemented with 10% fetal bovine serum (FBS) (v/v), L-glutamine (2 mM), sodium pyruvate (1 mM), HEPES (10 mM), non-essential amino acids, and bovine insulin (1 ug/mL). Ten days prior to the assay, the MCF-7 cells are switched to maintenance medium supplemented with 10% dextran-coated charcoal stripped fetal bovine serum (DCC-FBS) assay medium in place of the 10% FBS to deplete internal stores of estrogen. MCF-7 cells are removed from the maintenance flasks using a cell dissociating medium (Ca/Mg free HBSS; phenol-red free) supplemented with 10 mM HEPES and 2 mM EDTA. Cells are washed twice with the assay medium and adjusted to 80,000 cells/mL. Approximately 100 uL (8,000 cells) are added to a flat-bottomed micro culture well (Costar 3596) and incubated at 37° C. in a 5% $CO_2$ humidified incubator for 48 hours to allow cell adherence and equilibrium after transfer. Serial dilutions of the compounds of formula I or DMSO as a diluent control are prepared in assay medium and 50 uL transferred to triplicate micro cultures followed by 50 uL of assay medium for a final volume of 200 uL. After an additional 48 hours of incubation, the micro cultures are pulsed with tritiated thymidine (1 uCi/well) for 4 hours. Cultures are terminated by freezing at −70° C. for 24 hours followed by thawing and harvesting of micro cultures using a Skatron Semiautomatic Cell Harvester. Samples are counted by liquid scintillation. Fifty percent inhibitory concentration of the test drugs ($IC_{50}$) are determined versus the control (DMSO).

B. DMBA-Induced Mammary Tumor Inhibition Test Procedure

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between the groups.

Compounds of formula I are administered either through intraperitoneal injections in 2% acacia, or orally. Orally administered compounds are either dissolved or suspended in 0.2 mL of corn oil. Each treatment, including acacia and corn oil control treatments, is administered once daily to each animal. Following the initial tumor measurement and selection of test animals, tumors are measured each week by the above mentioned method. The treatment and measurements of animals continue for 3 to 5 weeks at each time the areas of the tumors are determined. For each compound and control, the change in the mean tumor area is determined.

The compounds of formula I would be potent inhibitors of cancer cell growth and tumor size in the above test procedures. Thus, the compounds of formula I would show a potential for the treatment or prevention of breast cancer.

Uterine Fibrosis

A. First Test Procedure

One hundred women, who have been diagnosed as suffering from uterine fibroid disease, are chosen for this study. These women are between the ages of 25–40 years of age and are in general good health. These women have been diagnosed as having uterine fibroid disease by the usual techniques, which include CT and MRI imaging, hysteroscopy, hysterosalpingography, ultrasound, or laparoscopy. These women would be evaluated by the attending physician as being good candidates for surgical intervention to remove the myomas. Excluded from this study would be those women, who are taking any form of hormonal therapy for this or other reasons.

Fifty women would receive 20–100 mg of a compound of formula I per day and fifty women would receive a matched placebo. The study would continue for three months. At the end of the study period, each patient would evaluated by parameters above and status of the fibrosis determined. This study would demonstrate that the patients receiving a compound of formula I would have smaller myomas than at the initiation of the study. The control would show no change or an increase in the size of the myomas during the study time.

B. Second Test Procedure

1. Induction of Fibroid Tumors in Guinea Pigs

Prolonged estrogen stimulation is used to induce leiomyomata in sexually mature female guinea pigs. Animals are dosed with estradiol 3–5 times per week by injection, for 2–4 months or until tumors arise. Treatments consisting of a compound of formula I or vehicle are administered daily for 3–16 weeks. Animals are sacrificed at the end of time period and the uteri harvested. Number and size of the tumors are determined both the control group and the treatment group. Animals, which had been treated with a compound of formula I, would have fewer and smaller leiomyomata than the control group.

2. Implantation of Human Tumor Tissue in Nude Mice

Tissue from human leiomyomas are implanted into the peritoneal cavity of sexually mature, female, nude mice (immune deficient). Exogenous estrogen (estradiol, time-release pellets) is supplied to the mice to stimulate the growth of the implants. The test group receives a compound of formula I in corn oil by gastric gavage once a day. The control group receives only corn oil by gastric gavage once a day. The dosing continues for 3–16 weeks. Growth of the implants is measured by metric caliper each week. The compounds of formula I would inhibit the growth of the tumor implants relative to the control.

Activity in at least one of the above tests would indicate the compounds of formula I have the potential to treat or prevent uterine fibroid disease.

Endometriosis Test Procedure

One hundred women suffering from diagnosed endometriosis would be chosen for the study. These women should be in general good health. Women receiving hormonal therapy (estrogens, progestins, GnRH, or danazol) for any reason would be excluded from the study.

Since endometriosis is idiosyncratic, diagnosis must be carefully made on each individual and a variety of parameters must be evaluated. Analysis of each of these individual parameters from the initial entry into the study to their final exit from the study must be carefully noted in order that the results of the clinical trial can be interpreted. The parameters listed may not all be essential in each case; however, there must be a least several defining factors. The parameters for endometriosis which may be monitored are: pelvic pain, CT, MRI, or ultrasound scans of the pelvic area, blood levels of CA125, and/or laparoscopy. As mentioned before, each individual will have a different spectrum of symptoms which need to be followed in that individual throughout the course of the study.

Fifty women would receive 20–100 mg of a compound of formula I per day and fifty women would receive a matched placebo. The study would continue for three months. At the end of the study period, each patient would evaluated by parameters above and status of the endometriosis determined. This study would demonstrate that the patients receiving a compound of formula I would have fewer symptoms and/or smaller endometrial masses than at the initiation of the study. The control would show no change or an increase in the size of the endometrial masses and little or no change in their symptoms during the study time.

Restenosis Test Procedure

Compounds of this invention have the capacity of inhibiting aortal smooth muscle cell proliferation, an experimental model for the inhibition of restenosis. The assay system described in U.S. Pat. No. 5,457,113 may be employed. The compounds of the instant invention would be shown to be potent inhibitors of aortal smooth muscle cell proliferation and therefore, would potentially be useful in inhibiting restenosis in the clinical setting.

From the foregoing, it will be seen that this invention is one well adapted to attain all the ends hereinabove set forth together with advantages that are inherent to the invention. It will be understood that certain features and subcombinations are of utility and can be employed without reference to other features and subcombinations. This is contemplated by and within the scope of the claims. Because many possible embodiments can be made of the invention without departing from the scope thereof, it is to be understood that all matter herein set forth is to be interpreted as illustrative and not in a limiting sense.

We claim:

1. A compound of formula I

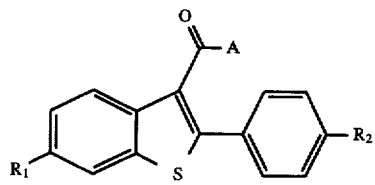

wherein:

$R_1$ is —H, —OH, —O($C_1$-$C_4$ alkyl), —C—CO—($C_1$-$C_6$ alkyl), —O—CO—O($C_1$-$C_6$ alkyl), —O—CO—Ar where Ar is phenyl or optionally substituted phenyl, —O—CO—O—Ar where Ar is phenyl or optionally substituted phenyl, or —OSO$_2$—($C_4$-$C_6$ alkyl);

$R_2$ is —H, —OH, —O($C_1$-$C_4$ alkyl), —O—CO—($C_1$-$C_6$ alkyl), —O—CO—O($C_1$-$C_6$ alkyl), —O—CO—Ar where Ar is phenyl or optionally substituted phenyl, —O—CO—O—Ar where Ar is phenyl or optionally substituted phenyl, —OSO$_2$—($C_4$-$C_6$ alkyl), —F, —Cl, or Br;

A is

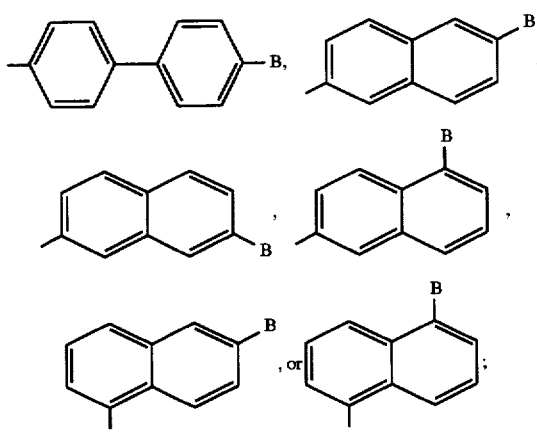

B is —OCH$_2$CH$_2$NR$_3$R$_4$;

R$_3$ and R$_4$ each are independently C$_1$–C$_4$ alkyl, or combine to form, with the nitrogen to which they are attached, piperidinyl, pyrrolidinyl, methylpyrrolidinyl, dimethylpyrrolidinyl, or hexamethyleneimino;

or a pharmaceutically acceptable salt or solvate thereof.

2. A compound according to claim 1 wherein R$_1$ and R$_2$ are —OH.

3. A compound according to claim 1 wherein A is biphenyl or naphth-2-yl.

4. A compound according to claim 1 wherein R$_3$ and R$_4$ combine to form, with the nitrogen to which they are attached, piperidinyl, pyrrolidinyl, or hexamethyleneimino.

5. A compound according to claim 1 wherein R$_3$ and R$_4$ combine to form, with the nitrogen to which they are attached, piperidinyl.

6. A compound according to claim 1 selected from the group consisting of
[2-(4-Methoxyphenyl)-6-methoxybenzo[b]thien-3-yl][4'-[2-(1-piperidinyl)ethoxy]biphenyl-4-yl]methanone,
[2-(4-Hydroxyphenyl)-6-hydroxybenzo[b]thien-3-yl][4'-[2-(1-piperidinyl)ethoxy]biphenyl-4-yl]methanone,
[2-(4-Methoxyphenyl)-6-methoxybenzo[b]thien-3-yl][6-[2-(1-piperidinyl)ethoxy]naphth-2-yl]methanone, and
[2-(4-Hydroxyphenyl)-6-hydroxybenzo[b]thien-3-yl][6-[2-(1-piperidinyl)ethoxy]naphth-2-yl]methanone.

7. A compound according to claim 1 wherein said salt thereof is the hydrochloride salt.

8. A pharmaceutical formulation comprising a compound according to claim 1 in combination with a pharmaceutically acceptable carrier, diluent, or excipient.

9. A method of inhibiting estrogen deprivation comprising administering to a patient in need thereof an effective amount of a compound of claim 1.

10. A method according to claim 9 wherein said estrogen deprivation is due to menopause or ovariectomy.

11. A method according to claim 9 wherein a pathology caused by the deprivation of estrogen leads to postmenopausal syndrome.

12. A method according to claim 9 wherein a pathology caused by the deprivation of estrogen leads to osteoporosis or cardiovascular disease.

13. A method according to claim 12 wherein said cardiovascular disease is hyperlipidemia.

14. A method for the inhibition of estrogen-dependent cancer comprising administering to a human in need thereof an effective amount of a compound of claim 1, or a pharmaceutically acceptable salt or solvate thereof.

15. A method according to claim 14 wherein said estrogen-dependent cancer is selected from the group consisting of breast and uterine cancer.

16. A method for the inhibition of restenosis comprising administering to a human in need thereof an effective amount of a compound of claim 1, or a pharmaceutically acceptable salt or solvate thereof.

17. A method for the inhibition of aortal smooth muscle cell proliferation comprising administering to a human in need thereof an effective amount of a compound of claim 1, or a pharmaceutically acceptable salt or solvate thereof.

18. A method for the inhibition of uterine fibroid disease comprising administering to a woman in need thereof an effective amount of a compound of claim 1, or a pharmaceutically acceptable salt or solvate thereof.

19. A method for the inhibition of endometriosis comprising administering to a woman in need thereof an effective amount of a compound of claim 1, or a pharmaceutically acceptable salt or solvate thereof.

* * * * *